(12) United States Patent
Ho et al.

(10) Patent No.: US 11,957,722 B2
(45) Date of Patent: Apr. 16, 2024

(54) ANTI-AGING COMPOSITION AND USE THEREOF FOR PREVENTING AGING

(71) Applicant: GLAC BIOTECH CO., LTD, Tainan (TW)

(72) Inventors: Hsieh-Hsun Ho, Tainan (TW); Yi-Wei Kuo, Tainan (TW); Wen-Yang Lin, Tainan (TW); Jia-Hung Lin, Tainan (TW); Yen-Yu Huang, Tainan (TW); Chi-Huei Lin, Tainan (TW); Shin-Yu Tsai, Tainan (TW)

(73) Assignee: GLAC BIOTECH CO., LTD, Tainan (TW)

(*) Notice: Subject to any disclaimer, the term of this patent is extended or adjusted under 35 U.S.C. 154(b) by 132 days.

(21) Appl. No.: 17/688,024

(22) Filed: Mar. 7, 2022

(65) Prior Publication Data
US 2023/0173000 A1 Jun. 8, 2023

(30) Foreign Application Priority Data
Dec. 8, 2021 (TW) .................................. 110145942

(51) Int. Cl.
| | |
|---|---|
| *A61K 35/747* | (2015.01) |
| *A23L 33/135* | (2016.01) |
| *A61K 8/99* | (2017.01) |
| *A61Q 19/08* | (2006.01) |
| *C12N 1/20* | (2006.01) |
| *C12R 1/225* | (2006.01) |

(52) U.S. Cl.
CPC .......... *A61K 35/747* (2013.01); *A23L 33/135* (2016.08); *A61K 8/99* (2013.01); *A61Q 19/08* (2013.01); *C12N 1/205* (2021.05); *C12R 2001/225* (2021.05)

(58) Field of Classification Search
CPC ....... A61K 35/747; A61K 8/99; A23L 33/135; A61Q 19/08; C12N 1/205; C12R 2001/225
See application file for complete search history.

(56) References Cited

U.S. PATENT DOCUMENTS

2017/0326186 A1* 11/2017 Mogna ..................... C12N 1/20
2021/0052676 A1* 2/2021 Hsieh .................. A61K 35/747

FOREIGN PATENT DOCUMENTS

RU         2261909 C1 * 10/2005

OTHER PUBLICATIONS

Hwang et al. Lactobacillus casei Extract Induces Apoptosis in Gastric Cancer by Inhibiting NF-κB and mTOR-Mediated Signaling. Integrative Cancer Therapies. Apr. 13, 2012 (Year: 2012).*

* cited by examiner

*Primary Examiner* — Iqbal H Chowdhury
(74) *Attorney, Agent, or Firm* — Locke Lord LLP; Tim Tingkang Xia, Esq.

(57) ABSTRACT

The present invention discloses an anti-aging composition, which includes: (a) isolated lactic acid bacterial strains or a fermented product thereof; and (b) an excipient, a diluent, or a carrier; wherein the isolated lactic acid bacterial strains include: *Bifidobacterium bifidum* VDD088 strains, *Bifidobacterium breve* Bv-889 strains, and *Bifidobacterium longum* BLI-02 strains. The present invention further provides a method for preventing aging by administering the foregoing anti-aging composition to a subject in need thereof.

7 Claims, 6 Drawing Sheets

ANTI-AGING COMPOSITION AND USE THEREOF FOR PREVENTING AGING

CROSS REFERENCE

This non-provisional application claims priority of Taiwan Invention Patent Application No. 110145942, filed on Dec. 8, 2021, the contents thereof are incorporated by reference herein.

FIELD OF THE INVENTION

The present invention is directed to an anti-aging composition, and more particularly to an anti-aging composition including lactic acid bacteria or the fermented product thereof. Also, the present invention is related to a method for preventing aging.

BACKGROUND OF THE INVENTION

Aging is a physiological decline phenomenon, which is also universal, progressive, cumulative, and deleterious. However, based on individual difference, this phenomenon can't be explained with any single or simple mode. It is found that reactive oxygen species are closely related to human aging. Generally, reactive oxygen species can destruct intracellular molecules in a body, e.g., DNA, protein, or lipid, so that the gradual loss of physiological functions occurs to trigger disease and organ senescence. It is also found that oxidation materials are related to cardiovascular disease, cancer, and aging. Some research further demonstrates that reactive oxygen species are one of the major factors to trigger organ senescence. Accordingly, it is one of the major issues in the anti-aging field to search novel anti-oxidation materials for aging prevention.

It is proven from some research that resveratrol exhibits an excellent anti-oxidation property and executes an aging-prevention function in an animal experiment model. However, resveratrol has potential side effects, and it is clinically found that taking resveratrol at a high dosage (from 2.5 g/day to 5.0 g/day) can lead to nausea, abdominal bloating, abdominal discomfort, or diarrhea. Additionally, resveratrol may have an anti-coagulation property, may interfere with enzymes involved in drug metabolism in a liver, e.g., cytochrome P450 or CYP1A2, to interfere with drug action, or may trigger unknown risk. Therefore, it is suitable to consult a doctor or a pharmacist before taking resveratrol. It is also found that resveratrol has a slight estrogenic property in an animal experiment model, and thus someone sensitive to estrogen, e.g., a breast cancer patient, an ovarian cancer patient, or a cervical cancer patient, should avoid taking resveratrol.

Generally, the activation of an intracellular p53/p21 signal transduction pathway or the upregulation of genes therein can induce cell cycle arrest to lead to cellular senescence. As described in Nature Aging volume 1, pages 962-973 (2021), after clearing senescent cells with high expression of P21 gene in senescent mice, the body function can recover. In other words, repressing P21 gene expression in senescent cells is helpful for aging prevention.

Probiotics are significant symbiotic bacteria in a human body. Based on strain difference and species difference, probiotics may have various biological functions, e.g., adjusting the microflora in a gastrointestinal tract and the function of the gastrointestinal tract, adjusting the blood glucose, strengthening the immune system, anti-oxidation, and anti-fatigue. Additionally, some bacterial strains individually have various different functions. For example, a *Lactobacillus rhamnosus* GG (LGG) strain is the strain which is recently researched by the most people and is able to execute various different functions, e.g., balancing or improving the function of a gastrointestinal tract, strengthening the immune system in a human body, preventing or treating diarrhea, preventing the respiratory tract infection, excreting the toxins, and preventing dental caries. The finding of these functional bacterial strains is helpful for enhancing human health. It is also lately found that some probiotic strains have the activity of anti-oxidation.

Geriatric health care is an issue recently valued by global authorities, and therefore it is important to develop an anti-aging supplement which is safe and can be chronically taken. Generally, it is safe to take probiotics, and thus it is an urgent objective to search probiotic bacterial strains having the anti-aging function.

SUMMARY OF THE INVENTION

The present invention is made based on the discovery that a composition comprising lactic acid bacterial strains or the fermented product thereof is proven to exhibit the anti-aging activity in vitro and in vivo. Accordingly, said composition can be in the form of a food, a pharmaceutical, or a cosmetic to execute the anti-aging physiological function.

The present invention discloses an anti-aging composition, which includes: (a) isolated lactic acid bacterial strains or a fermented product thereof; and (b) an excipient, a diluent, or a carrier; wherein the isolated lactic acid bacterial strains include: *Bifidobacterium bifidum* VDD088 strains deposited at the China General Microbiological Culture Collection Center with an accession No. CGMCC 15211, *Bifidobacterium breve* Bv-889 strains deposited at the China General Microbiological Culture Collection Center with an accession No. CGMCC 16145, and *Bifidobacterium longum* BLI-02 strains deposited at the China General Microbiological Culture Collection Center with an accession No. CGMCC 15212.

The present invention also discloses a method for preventing aging, which includes step(s) of: administering an anti-aging composition to a subject in need thereof, the anti-aging composition including: (a) isolated lactic acid bacterial strains or a fermented product thereof; and (b) an excipient, a diluent, or a carrier; wherein the isolated lactic acid bacterial strains include: *Bifidobacterium bifidum* VDD088 strains deposited at the China General Microbiological Culture Collection Center with an accession No. CGMCC 15211, *Bifidobacterium breve* Bv-889 strains deposited at the China General Microbiological Culture Collection Center with an accession No. CGMCC 16145, and *Bifidobacterium longum* BLI-02 strains deposited at the China General Microbiological Culture Collection Center with an accession No. CGMCC 15212.

DETAILED DESCRIPTION OF THE INVENTION

The detailed description and preferred embodiments of the invention will be set forth in the following content, and provided for people skilled in the art to understand the characteristics of the invention.

The freeze-dried culture of each lactic acid bacterial strain according to the present invention is deposited at the China Center for Type Culture Collection in Wuhan University, Wuhan City, China or deposited at the China General Microbiological Culture Collection Center in No. 3, No. 1 Courtyard, Beichen West Road, Chaoyang District, Beijing City, China. Deposition information is listed in Table 1 below.

TABLE 1

Deposition information of lactic acid bacterial strains

| Strain | Classification | Accession number | Deposition date |
| --- | --- | --- | --- |
| VDD088 | Bifidobacterium bifidum | CGMCC 15211 | Jan. 15, 2018 |
| Bv-889 | Bifidobacterium breve | CGMCC 16145 | Jul. 23, 2018 |
| BLI-02 | Bifidobacterium longum | CGMCC 15212 | Jan. 15, 2018 |
| PL-02 | Lactobacillus plantarum | CGMCC 20485 | Aug. 6, 2020 |
| CP-9 | Bifidobacterium animalis subsp. lactis | CCTCC M2014588 | Nov. 24, 2014 |
| OLP-01 | Bifidobacterium longum subsp. longum | CGMCC 17345 | Mar. 18, 2019 |

In this content, it is found that a *Bifidobacterium bifidum* VDD088 strain, a *Bifidobacterium breve* Bv-889 strain, a *Bifidobacterium longum* BLI-02 strain, a *Lactobacillus plantarum* PL-02 strain, a *Bifidobacterium animalis* subsp. *lactis* CP-9 strain, and a *Bifidobacterium longum* subsp. *longum* OLP-01 strain, as listed in Table 1, exhibit the anti-aging activity. Therefore, all bacterial strains listed or the fermented product thereof can be used for preventing aging.

An embodiment of the present invention provides an anti-aging composition, the composition including: (a) isolated lactic acid bacterial strains or a fermented product thereof; and (b) an excipient, a diluent, or a carrier; wherein the isolated lactic acid bacterial strains include: *Bifidobacterium bifidum* VDD088 strains deposited at the China General Microbiological Culture Collection Center with an accession No. CGMCC 15211, *Bifidobacterium breve* Bv-889 strains deposited at the China General Microbiological Culture Collection Center with an accession No. CGMCC 16145, and *Bifidobacterium longum* BLI-02 strains deposited at the China General Microbiological Culture Collection Center with an accession No. CGMCC 15212.

For strengthening the anti-aging activity, the isolated lactic acid bacterial strains further include: *Bifidobacterium animalis* subsp. *lactis* CP-9 strains deposited at the China Center for Type Culture Collection with an accession No. CCTCC M2014588, and *Lactobacillus plantarum* PL-02 strains deposited at the China General Microbiological Culture Collection Center with an accession No. CGMCC 20485.

For strengthening the anti-aging activity, the isolated lactic acid bacterial strains further include: *Bifidobacterium longum* subsp. *longum* OLP-01 strains deposited at the China General Microbiological Culture Collection Center with an accession No. CGMCC 17345.

Additionally, the excipient, the diluent, or the carrier may be a physiologically acceptable excipient, a physiologically acceptable diluent, or a physiologically acceptable carrier so that the composition may be used as a food composition or a cosmetic composition. On condition of the food composition, the physiologically acceptable excipient, the physiologically acceptable diluent, or the physiologically acceptable carrier may be a food, e.g., a milk product, a tea, a coffee, a candy (such as a buccal lozenge, a chewable lozenge, or a jelly candy), an energy drink, or any combination thereof; the milk product may be a fermented milk, a yogurt, a cheese, or a milk powder. On condition of the cosmetic composition, the physiologically acceptable excipient, the physiologically acceptable diluent, or the physiologically acceptable carrier may be (a) a liquid cosmetic, e.g., a shower gel, a shampoo, a hair conditioner, a toner, a fragrance, an essence, a lotion, or a moisturizing spray; (b) an emulsion cosmetic; (c) a cream cosmetic, e.g., a moisturizing cream, a cream foundation, a paste shampoo, an eye cream, a hand cream, a liquid mask, or a pomade; (d) a powder cosmetic, e.g., a face powder or a body powder; (e) a block cosmetic, e.g., a pressed powder; or (f) a bar cosmetic, e.g., a lipstick.

Moreover, the excipient, the diluent, or the carrier may be a pharmaceutically acceptable excipient, a pharmaceutically acceptable diluent, or a pharmaceutically acceptable carrier so that the composition may be used as a pharmaceutical composition. The pharmaceutical composition may be in an oral dosage form or in a topical dosage form, and an example of the oral dosage form is a tablet, a capsule, a solution, or a powder.

Further, the lactic acid bacterial strains may be individually a viable bacterial strain or a deactivated bacterial strain. On condition of the food composition, the cosmetic composition, or the pharmaceutical composition, the total bacterial count of the composition is preferably more than $10^6$ CFU, and more preferably more than $10^9$ CFU. In addition, the fermented product may comprise a fermented liquid containing deactivated bacterial strains, a fermented liquid without bacterial bodies, or a dried powder derived from any of the liquids. For example, the fermented liquid may be a fermented supernatant or a fermented whey solution. Based on the total weight of the composition, the dried powder derived from any of the liquids is preferably present in more than 0.5 wt %; the fermented liquid containing deactivated bacterial strains or the fermented liquid without bacterial bodies is preferably present in more than 2.5 wt %.

An embodiment of the present invention provides a method for preventing aging by administering the foregoing anti-aging composition to a subject in need thereof. In detail, after administration, the composition can scavenge free radicals, inhibit P21 gene expression, reduce protein carbonyl contents, enhance catalase activity and/or reduce 8-oxo-2'-deoxyguanosine contents in the body. As such, the need of preventing aging is satisfied. Preferably, the composition is administered to the subject at a total bacterial count from $10^6$ to $10^{10}$ CFU/kg of body weight of the subject/day so as to prevent aging. More preferably, the composition is administered to the subject at a total bacterial count from $8.3 \times 10^7$ to $3.4 \times 10^8$ CFU/kg of body weight of the subject/day.

Example 1: Morphological and Common Properties of Lactic Acid Bacterial Strains

The 16S ribosomal RNA (rRNA) sequencing and the API bacterial identification system are used to identify morphological properties of lactic acid bacterial strains. Morphological properties and common properties of lactic acid bacterial strains are listed in Table 2 below.

TABLE 2

Morphological and common properties of lactic acid bacterial strains

| Strains | Properties |
|---|---|
| *Bifidobacterium bifidum* VDD088 strain | 1. They are anaerobic and Gram-positive bacteria. They are non-sporogenous bacteria without catalase and oxidase and without mobility. They can survive in an obligate anaerobic environment, and the most suitable temperature for survival is $37 \pm 1°$ C. They are facultative heterofermentative bacteria and can't produce any gas during glucose metabolism.<br>2. They grow on a MRS agar medium in the form of a solid white circle. The bacterial bodies are in the form of a long rod, and two ends thereof have a dichotomous branch, e.g., a Y-shaped branch or a V-shaped branch. |
| *Bifidobacterium breve* Bv-889 strain | 1. They are anaerobic and Gram-positive bacteria. They are non-sporogenous bacteria without catalase and oxidase and without mobility. They can survive in an obligate anaerobic environment, and the most suitable temperature for survival is $37 \pm 1°$ C. They are facultative heterofermentative bacteria and can't produce any gas during glucose metabolism.<br>2. They grow on a MRS agar medium in the form of a solid white circle. The bacterial bodies are in the form of a short rod, and two ends thereof have a dichotomous branch, e.g., a Y-shaped branch or a V-shaped branch. |
| *Bifidobacterium longum* BLI-02 strain | 1. They are anaerobic and Gram-positive bacteria. They are non-sporogenous bacteria without catalase and oxidase and without mobility. They can survive in an obligate anaerobic environment, and the most suitable temperature for survival is $37 \pm 1°$ C. They are facultative heterofermentative bacteria and can't produce any gas during glucose metabolism.<br>2. They grow on a MRS agar medium in the form of a solid white circle. The bacterial bodies are in the form of a long rod, and two ends thereof have a dichotomous branch, e.g., a Y-shaped branch or a V-shaped branch. |
| *Lactobacillus plantarum* PL-02 strain | 1. They are facultative anaerobic bacteria, and can survive in an environment with a low or normal oxygen concentration. The suitable temperature for survival is from 10 to 45° C., and the most suitable temperature is from 30 to 35° C. However, they can still survive at a temperature close to the freezing point. The most suitable pH for growth ranges from pH 3.5 to pH 4.2, and the most suitable salinity tolerance for growth is from 13% to 15%.<br>2. They are in the shape of a linear rod, and two ends of their bodies are in the form of an ellipse. They have a width from 0.9 to 1.2 mm and a length from 3.0 to 8.0 mm. They usually appear alone, appear in pairs, or arrange in short chains. |
| *Bifidobacterium animalis* subsp. *lactis* CP-9 strain | 1. They are anaerobic and Gram-positive bacteria. They are non-sporogenous bacteria without catalase and oxidase and without mobility. They can survive in an obligate anaerobic environment, and the most suitable temperature for survival is $37 \pm 1°$ C. They are facultative heterofermentative bacteria and can't produce any gas during glucose metabolism.<br>2. They grow on a MRS agar medium in the form of a solid white circle. The bacterial bodies are in the form of a long rod, and two ends thereof have a dichotomous branch, e.g., a Y-shaped branch or a V-shaped branch. |
| *Bifidobacterium longum* subsp. *longum* OLP-01 strain | 1. They are anaerobic and Gram-positive bacteria. They are non-sporogenous bacteria without catalase and oxidase and without mobility. They can survive in an obligate anaerobic environment, and the most suitable temperature for survival is $37 \pm 1°$ C. They are facultative heterofermentative bacteria and can't produce any gas during glucose metabolism.<br>2. They grow on a MRS agar medium in the form of a solid white circle. The bacterial bodies are in the form of a long rod, and two ends thereof have a dichotomous branch, e.g., a Y-shaped branch or a V-shaped branch. |

Example 2: Cultivation of Lactic Acid Bacterial Strains

Bacterial strains are stored in 20% glycerol at −80° C. Before used, bacterial strains are activated using a MRS medium (DIFCO) containing 0.05% cysteine at 37° C. for 24 hours twice. All lactic acid bacterial strains used comprise: *Bifidobacterium bifidum* VDD088 strains, *Bifidobacterium breve* Bv-889 strains, *Bifidobacterium longum* BLI-02 strains, *Lactobacillus plantarum* PL-02 strains, *Bifidobacterium animalis* subsp. *lactis* CP-9 strains, and *Bifidobacterium longum* subsp. *longum* OLP-01 strains, all isolated from human gastrointestinal tracts. In an exemplary cultivation example, all lactic acid bacterial strains grow in a liquid medium containing 30 wt % milk and/or 1 wt % to 10 wt % soybean powders. In an exemplary cultivation example, all lactic acid bacterial strains grow in a liquid medium containing a carbon source and/or a nitrogen source, the carbon source comprises glucose, fructose, lactose, sucrose, maltose, galactose, mannose, trehalose, starch, molasses, potato starch, corn starch, malt extract, maltodextrin, or any combination thereof, and the nitrogen source comprised $(NH_4)_2SO_4$, $(NH_4)_3PO_4$, $NH_4NO_3$, $NH_4Cl$, casamino acid, urea, peptone, polypeptone, tryptone, meat extract, yeast extract, yeast powders, milk, soybean powders, whey, or any combination thereof. In an exemplary cultivation example, based on the total weight of the liquid medium, the entity of glucose and maltodextrin is present from 2 wt % to 5 wt %.

A fermented product is obtained through fermentation by lactic acid bacterial strains. In detail, a liquid medium is fermented by lactic acid bacterial strains to form a fermented liquid, then the fermented liquid is centrifuged, filtered, and pasteurized, and finally the fermented liquid is purified to form the fermented product. On demand, the fermented product is dried to fermented powders. No matter whether the fermented product is in the liquid form or in the powder form, it can be stored at a room temperature.

Example 3: Free Radical-Scavenging Activity Analysis

DPPH (di(phenyl)-(2,4,6-trinitrophenyl)iminoazanium) is a stable free radical, and a methanol solution containing DPPH free radicals has the highest absorbance at 517 nm. When DPPH free radicals react with an antioxidant, the antioxidant can scavenge the DPPH free radicals by donating hydrogen ions. As such, the DPPH solution loses its original violet color and the absorbance lowers.

Lactic acid bacterial strains to be tested and the fermented product thereof (the total bacterial count of $2\times10^9$ CFU; the OD value of 2.0) are mixed with a DPPH methanol solution at a ratio of 1:1. Streptococcus thermophiles L-243 strains (the total bacterial count of $2\times10^9$ CFU), which have no anti-oxidation ability, are used as a negative group and mixed with a DPPH methanol solution at the same ratio; distillation-distillation water is used as a blank group and mixed with a DPPH methanol solution at the same ratio. After uniformly mixed, the solution is placed at a dark place for 30 minutes for reaction. Then, after centrifuged at 12,000 rpm for 2 minutes at 4° C., 200 μL of the solution is added into a 96-well plate and the $OD_{517}$ value is measured. The free-radical scavenging efficacy is calculated following the formula below:

$$\text{Free-radical scavenging efficacy} = \frac{OD_{sample} - OD_{blank}}{OD_{blank}} \times 100\%;$$

wherein the $OD_{sample}$ indicates an $OD_{517}$ value measured from the tested sample, and the $OD_{blank}$ indicates an $OD_{517}$ value measured from the blank group.

Figure 1:
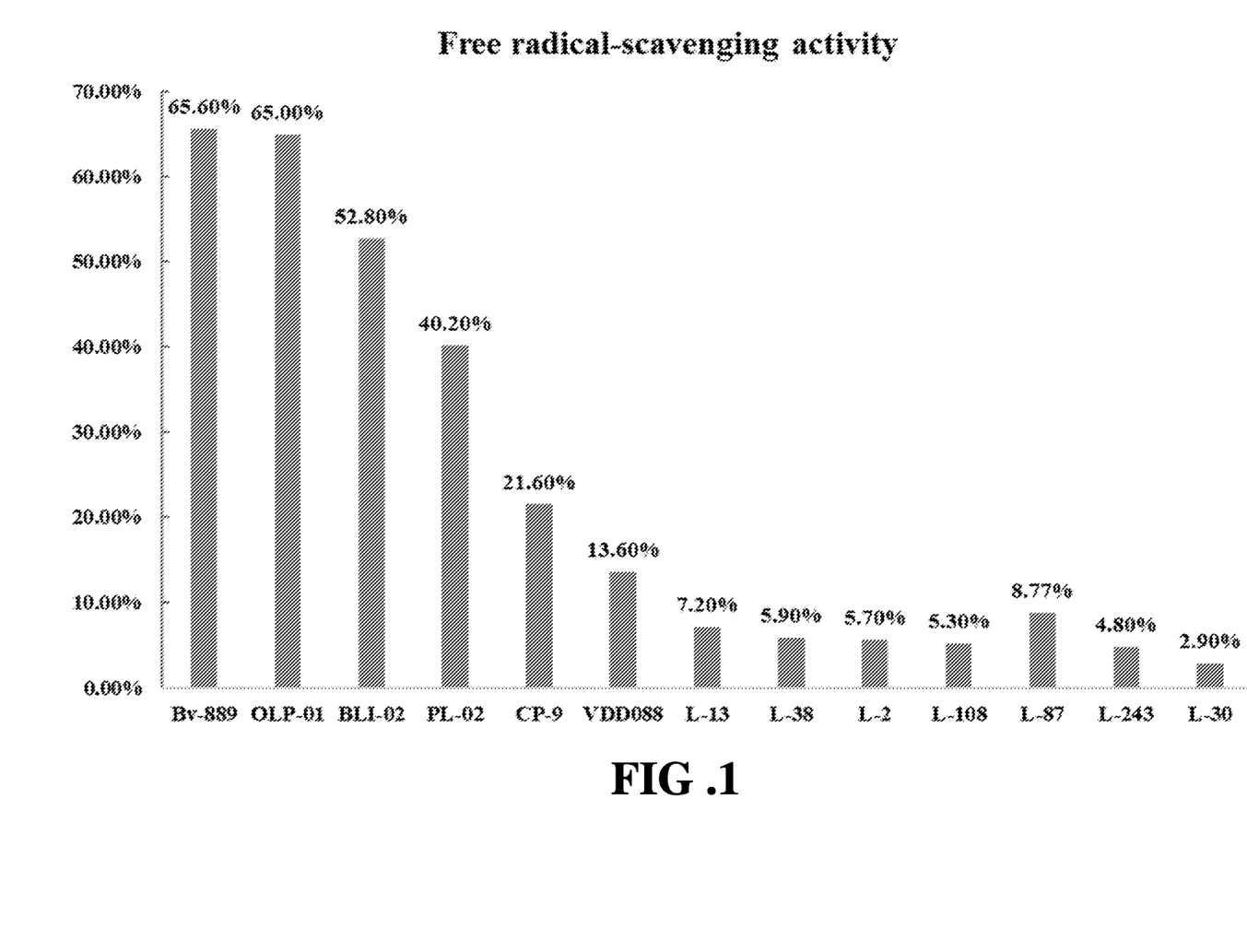
FIG. 1 is a graph related to the result of free radical-scavenging activity analysis illustrating effects of various bacterial strains on free radical scavenging.

As shown in FIG. 1, as compared with other kinds of lactic acid bacterial strains, *Bifidobacterium breve* Bv-889 strains, *Bifidobacterium longum* subsp. *longum* OLP-01 strains, *Bifidobacterium longum* BLI-02 strains, *Lactobacillus plantarum* PL-02 strains, *Bifidobacterium animalis* subsp. *lactis* CP-9 strains, and *Bifidobacterium bifidum* VDD088 strains have relatively high activity to scavenge free radicals.

Example 4: Ferric-Ion Reduction Capacity Analysis

FRAP assay is the abbreviation for "ferric ion reducing antioxidant power assay" or "ferric reducing ability of plasma assay". Under a low pH environment, a ferrous ion reacts with tripyridyltriazine (TPTZ) to form a violet complex so that the anti-oxidation efficacy of the tested sample is determined. This assay is widely used for analyzing the anti-oxidation capacity of a food or a health food.

Figure 2:
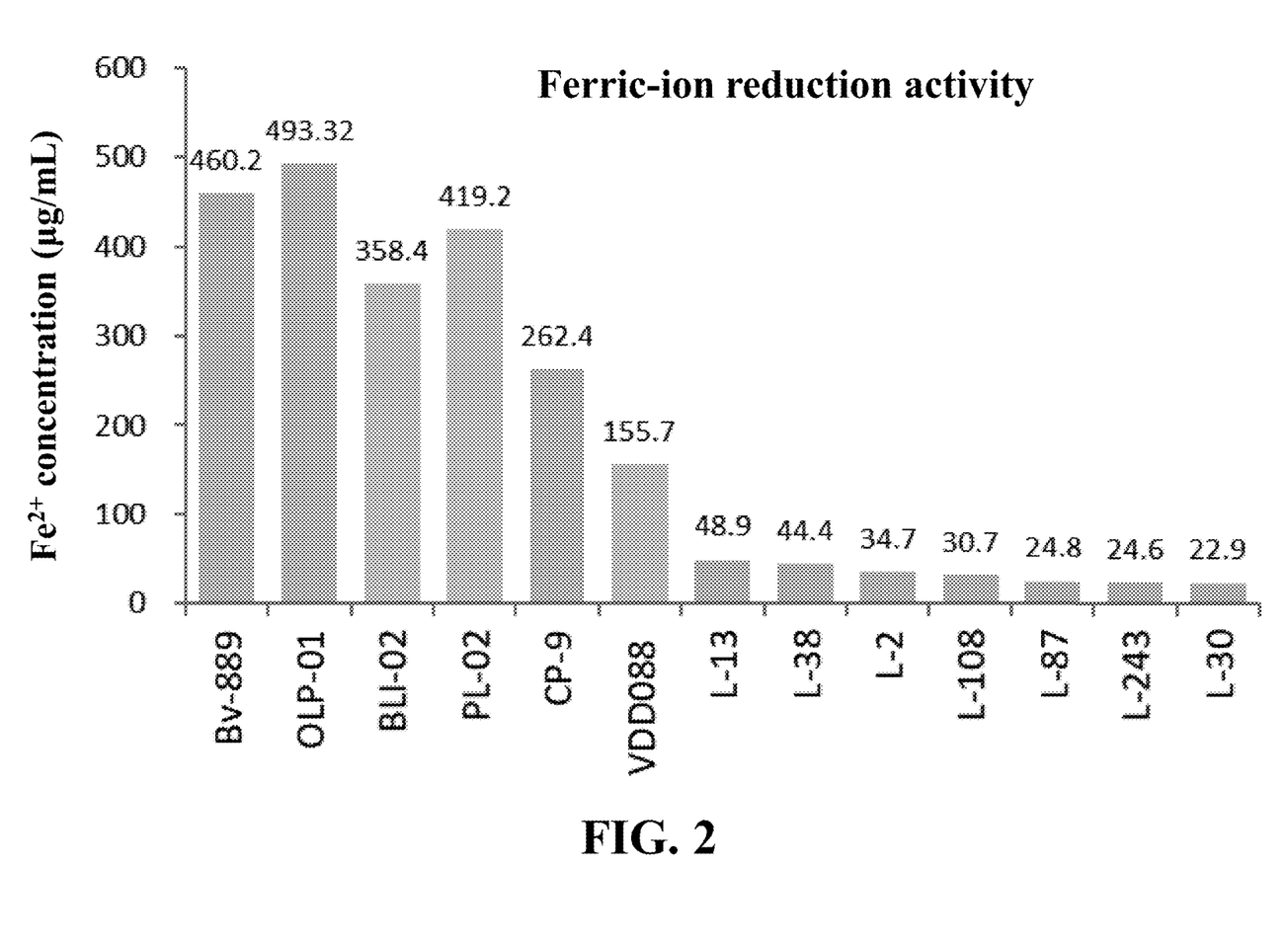
FIG. 2 is a graph related to the FRAP result illustrating effects of various bacterial strains on ferric-ion reduction.

Generally, an antioxidant reduces a $Fe^{3+}$-TRTZ complex to a violet $Fe^{2+}$-TRTZ complex under an acidic condition, and then the absorbance is measured at 593 nm to be an index for total anti-oxidation capacity. Further, the acidic condition can repress endogenous interfering substances. Since the sample to be tested has a concentration of ferric ions or ferrous ions lower than 10 μM, the ferric ions or the ferrous ions in the sample to be tested can't obviously interfere with the test result. Additionally, since the ferric ions or the ferrous ions in the reaction system can chelate TPTZ, a trace of the ferric ions or the ferrous ions in the sample to be tested usually have no effects on the test result. As shown in FIG. 2, as compared with other kinds of lactic acid bacterial strains, *Bifidobacterium breve* Bv-889 strains, *Bifidobacterium longum* subsp. *longum* OLP-01 strains, *Bifidobacterium longum* BLI-02 strains, *Lactobacillus plantarum* PL-02 strains, *Bifidobacterium animalis* subsp. *lactis* CP-9 strains, and *Bifidobacterium bifidum* VDD088 strains have relatively high activity to reduce ferric ions. That is, these kinds of bacterial strains have relatively high anti-oxidation activity.

Example 5: P21 Gene Expression Analysis

According to Probiotics Antimicrob Proteins. 2020 June; 12(2):563-576, mouse 3T3-L1 cells are used as a model, and these cells become senescent under oxidation caused by $H_2O_2$. In addition, these cells are treated with samples to be tested and the P21 gene expression therein is observed.

In detail, mouse 3T3-L1 cells are purchased from the Food Industry Research and Development Institute and incubated in a Dulbecco's modified Eagle's medium (DMEM) containing 10% FBS. Cells are incubated at 37° C. and a $CO_2$ concentration of 5%, and grew for 3 to 5 generations for further experiment.

Cells are seeded to a 6-well plate, each well containing $3\times10^4$ cells. After incubated for several days, cells are attached to the plate and have a confluence of 80%. 150 μM $H_2O_2$, as an oxidant, is added to each well to be incubated with cells for 3 hours, and then these cells are incubated with DMEM after washed with PBS. The foregoing step is performed again every 24 hours for three times. Meanwhile, during adding $H_2O_2$, samples to be tested are added to the wells to be incubated with the cells. After incubated with $H_2O_2$ for 3 hours, cells are washed with PBS and the same samples to be tested are added to the wells be incubated with the cells again. Finally, total RNA in these cells is extracted, and then real-time quantitative polymerase chain reaction (Q-PCR) is performed for analyzing P21 gene expression, wherein a primer pair for P21 gene comprise a forward primer 5'-tgcatccgtttcacccaacc-3' and a reverse primer 5'-tcatttttccaaagtgctattcagg-3' and another primer pair for GADPH gene, as an internal control, comprise a forward primer 5'-gaaggtgaaggtcggagt-3' and a reverse primer 5'-gaagatggtgatggatttc-3'.

Figure 3:
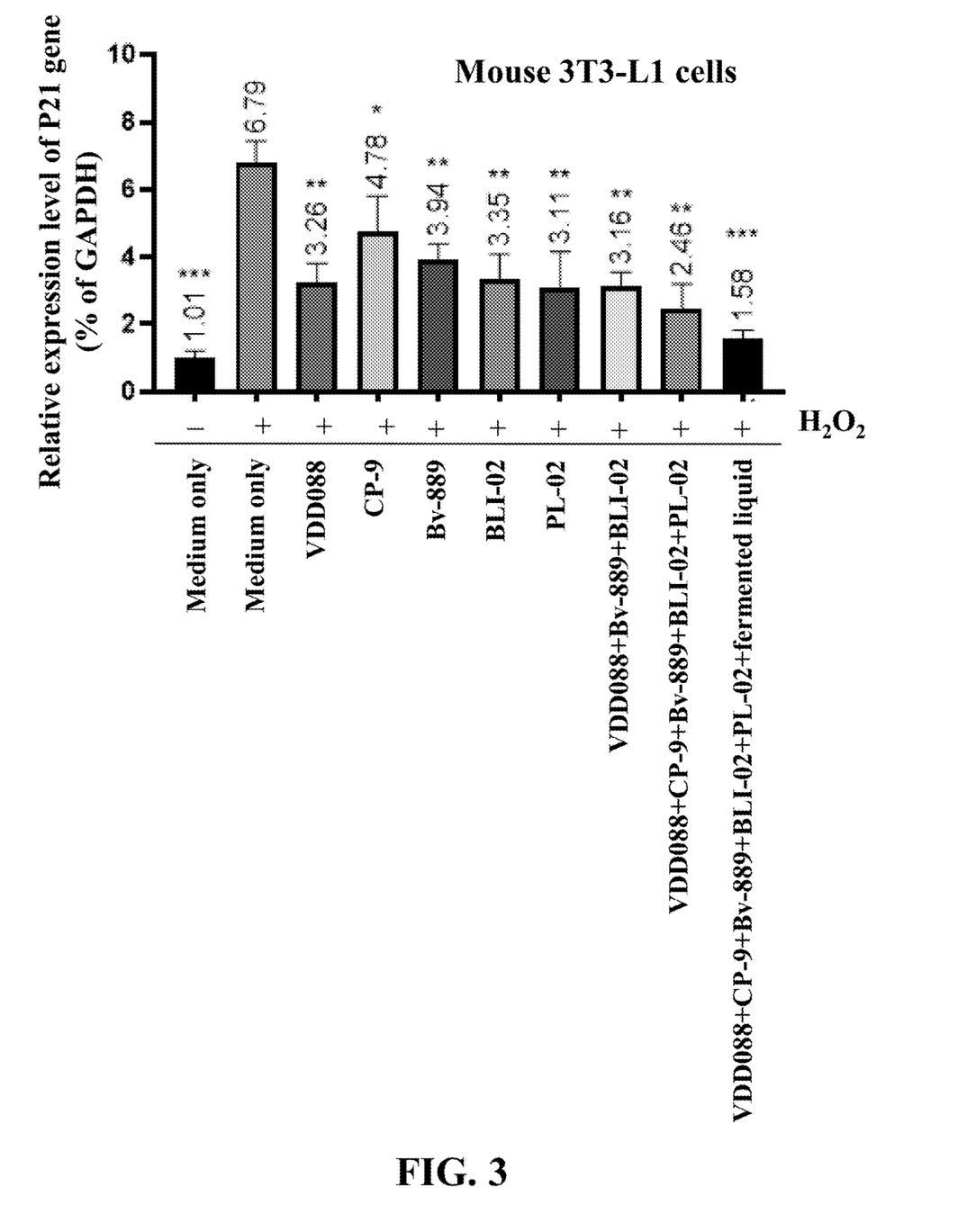
FIG. 3 is a graph related to the result of P21 expression illustrating effects of various samples on P21 expression in mouse 3T3-L1 cells.

As shown in FIG. 3, under $H_2O_2$ oxidation, cells treated with *Bifidobacterium bifidum* VDD088 strains (the total bacterial count of $2\times10^9$ CFU for each treatment), cells treated with *Bifidobacterium animalis* subsp. *lactis* CP-9 strains (the total bacterial count of $2\times10^9$ CFU for each treatment), cells treated with *Bifidobacterium breve* Bv-889 strains (the total bacterial count of $2\times10^9$ CFU for each treatment), cells treated with *Bifidobacterium longum* BLI-02 strains (the total bacterial count of $2\times10^9$ CFU for each treatment), cells treated with *Lactobacillus plantarum* PL-02 strains (the total bacterial count of $2\times10^9$ CFU for each treatment), and cells treated *Bifidobacterium longum* subsp.

*longum* OLP-01 strains (the total bacterial count of $2\times10^9$ CFU for each treatment) have a lower relative expression level of P21 gene than nontreated cells. This indicates these kinds of bacterial strains have ability to prevent aging.

As shown in FIG. 3, under $H_2O_2$ oxidation, cells co-treated with *Bifidobacterium bifidum* VDD088 strains, *Bifidobacterium breve* Bv-889 strains, and *Bifidobacterium longum* BLI-02 strains (the total bacterial count of $2\times10^9$ CFU for each treatment; the count ratio of all bacterial strain kinds of 1:1:1 for each treatment) have a lower relative expression level of P21 gene than cells merely treated with *Bifidobacterium bifidum* VDD088 strains, cells merely treated with *Bifidobacterium breve* Bv-889 strains, and cells merely treated with *Bifidobacterium longum* BLI-02 strains. This indicates the combination of *Bifidobacterium bifidum* VDD088 strains, *Bifidobacterium breve* Bv-889 strains, and *Bifidobacterium longum* BLI-02 strains can result in a synergy for aging prevention.

As shown in FIG. 3, under $H_2O_2$ oxidation, cells co-treated with *Bifidobacterium bifidum* VDD088 strains, *Bifidobacterium animalis* subsp. *lactis* CP-9 strains, *Bifidobacterium breve* Bv-889 strains, *Bifidobacterium longum* BLI-02 strains, and *Lactobacillus plantarum* PL-02 strains (the total bacterial count of $2\times10^9$ CFU for each treatment; the count ratio of all bacterial strain kinds of 1:1:1:1:1 for each treatment) have a lower relative expression level of P21 gene than cells merely treated with *Bifidobacterium bifidum* VDD088 strains, cells merely treated with *Bifidobacterium animalis* subsp. *lactis* CP-9 strains, cells merely treated with *Bifidobacterium breve* Bv-889 strains, cells merely treated with *Bifidobacterium longum* BLI-02 strains, and cells merely treated with *Lactobacillus plantarum* PL-02 strains. This indicates the combination of *Bifidobacterium bifidum* VDD088 strain, *Bifidobacterium animalis* subsp. *lactis* CP-9 strains, *Bifidobacterium breve* Bv-889 strains, *Bifidobacterium longum* BLI-02 strains, and *Lactobacillus plantarum* PL-02 strains can result in a synergy for aging prevention.

As shown in FIG. 3, under $H_2O_2$ oxidation, cells co-treated with *Bifidobacterium bifidum* VDD088 strains, *Bifidobacterium animalis* subsp. *lactis* CP-9 strains, *Bifidobacterium breve* Bv-889 strains, *Bifidobacterium longum* BLI-02 strains, *Lactobacillus plantarum* PL-02 strains (the total bacterial count of $2\times10^9$ CFU for each treatment; the count ratio of all bacterial strain kinds of 1:1:1:1:1 for each treatment), and a fermented liquid of these bacterial strains have a lower relative expression level of P21 gene than cells co-treated with *Bifidobacterium bifidum* VDD088 strains, *Bifidobacterium animalis* subsp. *lactis* CP-9 strains, *Bifidobacterium breve* Bv-889 strains, *Bifidobacterium longum* BLI-02 strains, and *Lactobacillus plantarum* PL-02 strains. This indicates the fermented liquid of these bacterial strains has ability to prevent aging.

Example 6: Anti-Aging Analysis in Mice

The protein carbonyl content, the catalase (CAT) activity, and the mitochondria 8-oxo-2'-deoxyguanosine (8OHdG) content are important indexes for estimating tissue aging. All indexes are used to analyze the anti-aging property of samples to be tested in mice as described below.

10-month-old mice are divided into 6 groups, each group containing 4 mice. The dosage for administering lactic acid bacteria is determined based on "Estimating the maximum safe starting dose in initial clinical trials for therapeutics in adult healthy volunteers" established by the U.S. Food and Drug Administration (FDA) in 2005. The blank control group are merely fed with mouse feed; the group with resveratrol administration are not only fed with mouse feed, but also fed with resveratrol at a dosage of 20.5 mg/kg of mouse body weight/day; the group with low dose lactic acid bacterial strains administration are not only fed with mouse feed, but also fed with a mixture of lactic acid bacterial strains at a dosage of $1.03\times10^9$ CFU/kg of mouse body weight/day; the group with low dose lactic acid bacterial strains and fermented product administration are not only fed with mouse feed, but also fed with a mixture of lactic acid bacterial strains at a dosage of $1.03\times10^9$ CFU/kg of mouse body weight/day and a fermented product at a dosage of 20.5 mg/kg of mouse body weight/day; the group with high dose lactic acid bacterial strains administration are not only fed with mouse feed, but also fed with a mixture of lactic acid bacterial strains at a dosage of $4.1\times10^9$ CFU/kg of mouse body weight/day; the group with high dose lactic acid bacterial strains and fermented product administration are not only fed with mouse feed, but also fed with a mixture of lactic acid bacterial strains at a dosage of $4.1\times10^9$ CFU/kg of mouse body weight/day and a fermented product at a dosage of 20.5 mg/kg of mouse body weight/day. The mixture of lactic acid bacterial strains comprises *Bifidobacterium bifidum* VDD088 strains, *Bifidobacterium breve* Bv-889 strains, *Bifidobacterium longum* BLI-02 strains, *Lactobacillus plantarum* PL-02 strains, *Bifidobacterium animalis* subsp. *lactis* CP-9 strains, and *Bifidobacterium longum* subsp. *longum* OLP-01 strains, the count ratio of all bacterial strain kinds being 1:1:1:1:1:1. After fed for 6 straight weeks, the brains, the hearts, and the livers of mice are harvested for analyzing the senescence level in each group. The protein carbonyl content, the catalase activity, and the mitochondria 8-oxo-2'-deoxyguanosine (8OHdG) content are measured as described below:

1. After fed for 6 straight weeks, mice are sacrificed. Their organs including hearts, brains, and livers are harvested with surgical instruments, and then placed in Eppendorf tubes respectively. 200 μL of 0.4M perchloric acid is added to each tube to homogenize the organ with an ultrasonic homogenizer.

2. These indexes for estimating organ aging are determined by performing the experimental procedure provided in Protein Carbonyl Colorimetric Assay Kit (Cayman Chemical, 10005020), Catalase Assay Kit (Cayman Chemical, 707002), and 8-OHdG Check ELISA kit (JaICA, KOG200S/E) on the thus-obtained homogeneous solution containing each mouse organ.

Figure 4:
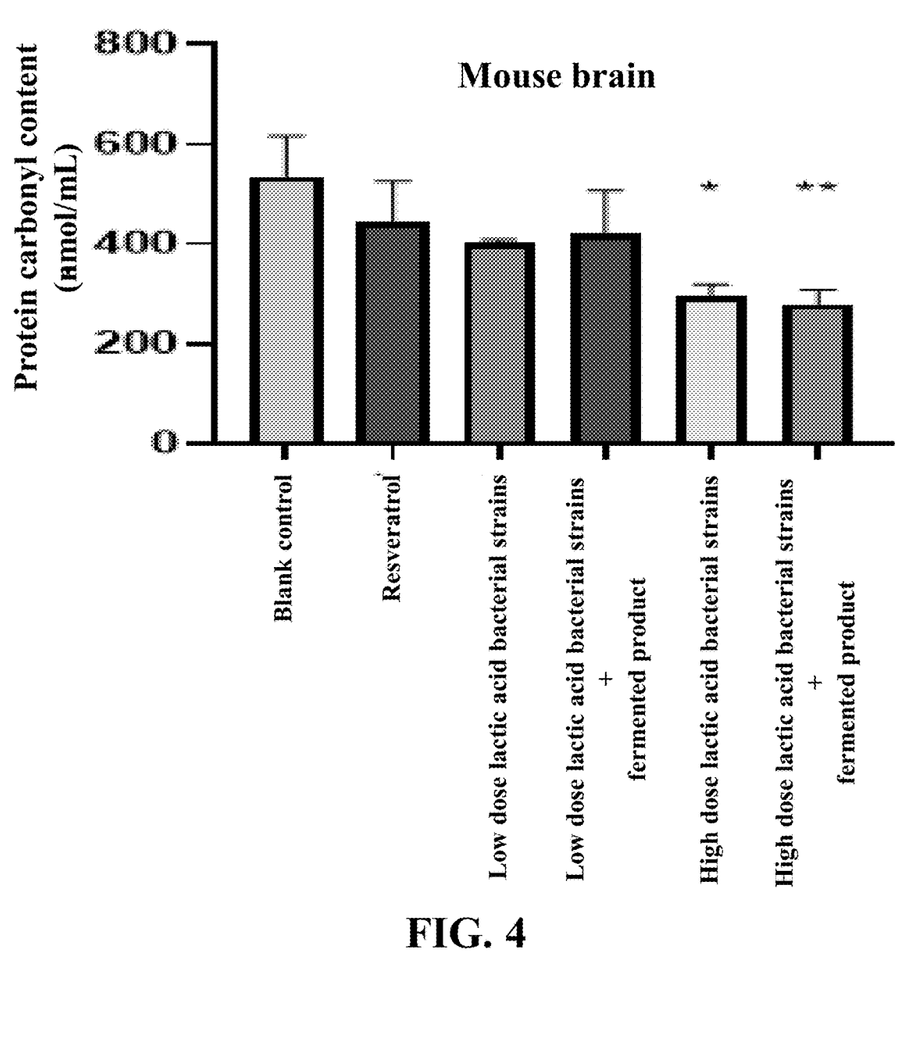
FIG. 4 is a graph related to the result of anti-aging analysis illustrating effects of various samples on protein carbonyl contents in mouse hindbrains.
Figure 5:
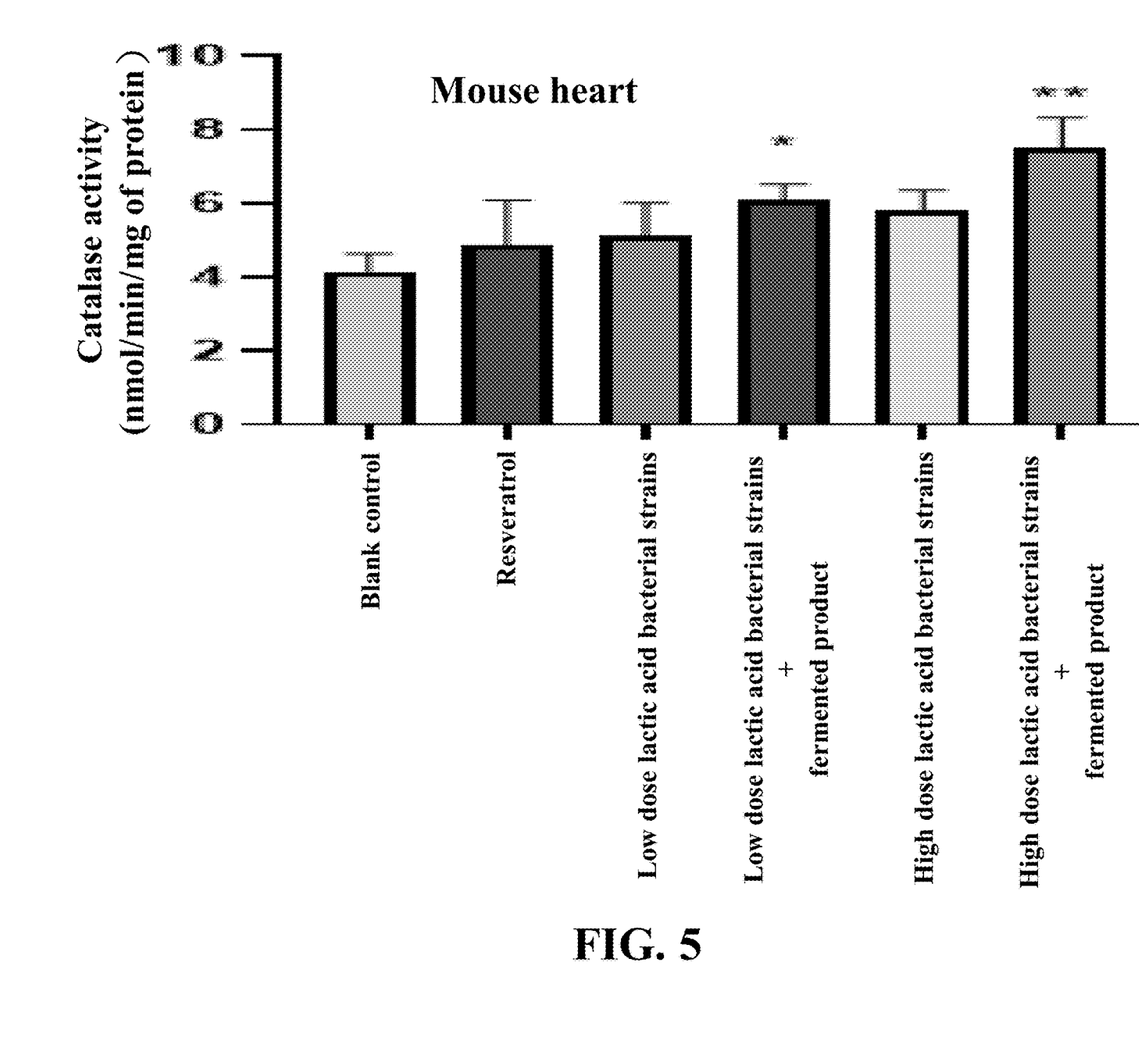
FIG. 5 is a graph related to the result of anti-aging analysis illustrating effects of various samples on catalase activity in mouse hearts.
Figure 6:
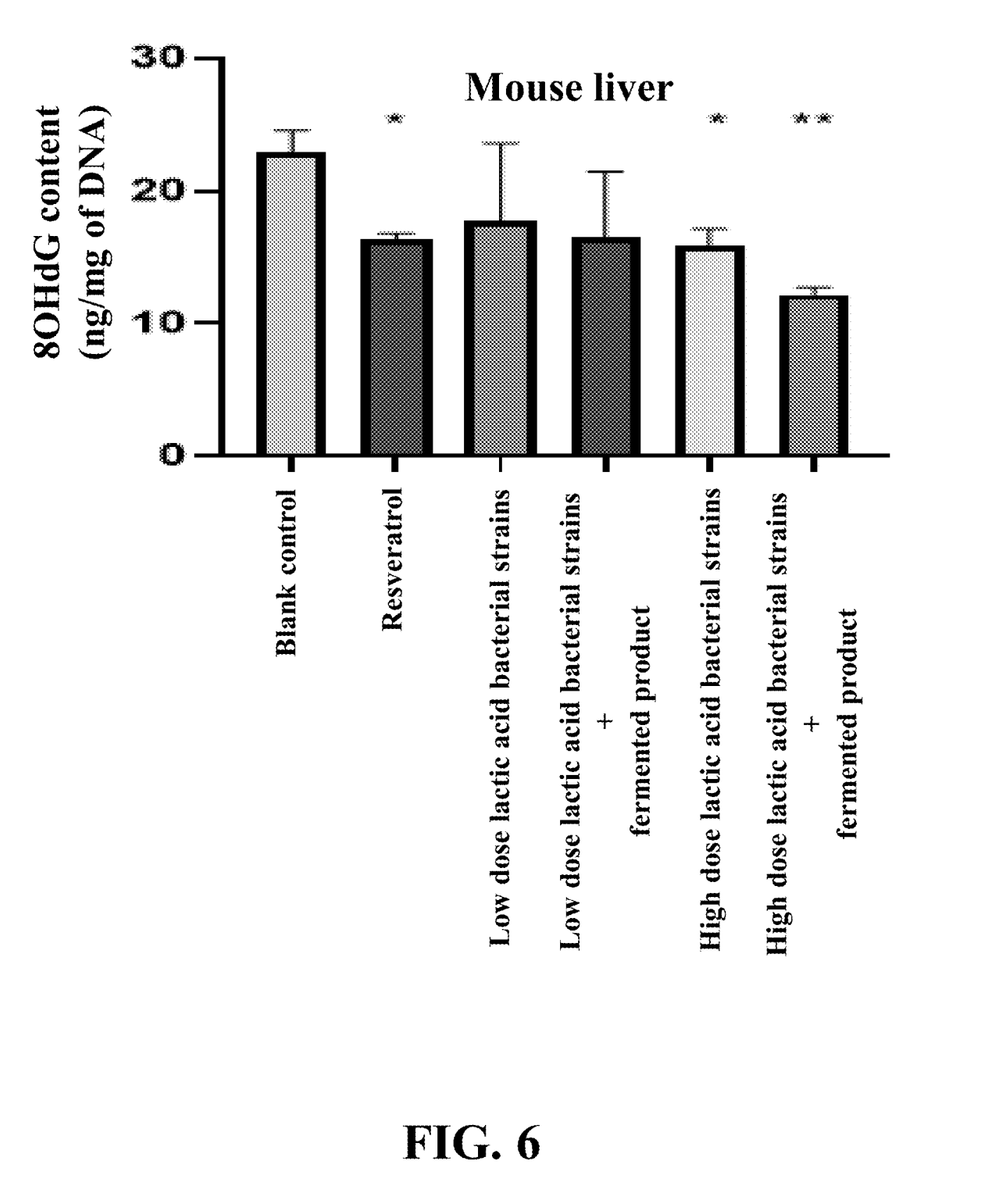
FIG. 6 is a graph related to the result of anti-aging analysis illustrating effects of various samples on 8-oxo-2'-deoxyguanosine contents in the mitochondria of mouse livers.

As shown in FIGS. 4 to 6, among all of the groups, the group with high dose lactic acid bacterial strains and fermented product administration have the lowest protein carbonyl content in brains, the highest catalase activity in hearts, and the lowest mitochondria 8-oxo-2'-deoxyguanosine content in livers. This indicates the combination of these lactic acid bacterial strains and their fermented liquid has the ability to prevent aging.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for anti-aging, comprising: administering a composition to a subject in need thereof; wherein the composition comprises: (a) isolated lactic acid bacterial strains; and (b) an excipient, a diluent, or a carrier; wherein the isolated lactic acid bacterial strains include: a *Bifido-*

*bacterium bifidum* VDD088 strain deposited at the China General Microbiological Culture Collection Center with an accession No. CGMCC 15211, a *Bifidobacterium breve* Bv-889 strain deposited at the China General Microbiological Culture Collection Center with an accession No. CGMCC 16145, a *Bifidobacterium longum* BLI-02 strain deposited at the China General Microbiological Culture Collection Center with an accession No. CGMCC 15212, a *Bifidobacterium animalis* sub sp. *lactis* CP-9 strain deposited at the China Center for Type Culture Collection with an accession No. CCTCC M2014588, and a *Lactobacillus plantarum* PL-02 strain deposited at the China General Microbiological Culture Collection Center with an accession No. CGMCC 20485.

2. The method for anti-aging as claimed in claim 1, wherein the isolated lactic acid bacterial strains further comprise: a *Bifidobacterium longum* subsp. *longum* OLP-01 strain deposited at the China General Microbiological Culture Collection Center with an accession No. CGMCC 17345.

3. The method for anti-aging as claimed in claim 1, wherein the composition is administered for scavenging free radicals, inhibiting P21 gene expression, reducing protein carbonyl contents, enhancing catalase activity, or reducing 8-oxo-2'-deoxyguanosine contents in a body of the subject.

4. The method for anti-aging as claimed in claim 1, wherein the composition is administered for inhibiting P21 gene expression in the subject.

5. The method for anti-aging as claimed in claim 1, wherein the composition is administered to the subject at a total bacterial count from $10^6$ to $10^{10}$ CFU/kg of body weight of the subject/day.

6. The method for anti-aging as claimed in claim 1, wherein the composition is administered to the subject at a total bacterial count from $8.3 \times 10^7$ to $3.4 \times 10^8$ CFU/kg of body weight of the subject/day.

7. The method for anti-aging as claimed in claim 1, wherein the lactic acid bacterial strains are individually a viable bacterial strain or a deactivated bacterial strain.

* * * * *